US005313824A

United States Patent [19]

Herguth et al.

[11] Patent Number: 5,313,824

[45] Date of Patent: May 24, 1994

[54] LUBRICATING OIL ANALYSIS METHOD AND KIT

[75] Inventors: William R. Herguth, Vallejo, Calif.; Peter Yates, Seattle, Wash.

[73] Assignee: Herguth Laboratories, Vallejo, Calif.

[21] Appl. No.: 954,116

[22] Filed: Sep. 30, 1992

[51] Int. Cl.[5] .......... G01N 33/28

[52] U.S. Cl. .......... 73/53.05

[58] Field of Search .......... 73/53.05, 53.07

[56] References Cited

U.S. PATENT DOCUMENTS

| | | | |
|---|---|---|---|
| 2,302,224 | 11/1942 | Jones . | |
| 2,622,471 | 12/1952 | Sparks . | |
| 2,946,216 | 7/1960 | Elliott et al. . | |
| 3,049,964 | 8/1962 | Miller et al. . | |
| 3,914,174 | 10/1975 | Fuchs | 210/31 |
| 4,596,137 | 6/1986 | Fisher et al. . | |
| 4,617,278 | 10/1986 | Reed | 436/60 |
| 4,751,187 | 6/1988 | Dickakian | 436/60 |
| 4,752,587 | 6/1988 | Dickakian | 436/60 |
| 4,781,892 | 11/1988 | Dickakian | 422/69 |
| 4,781,893 | 11/1988 | Dickakian | 422/69 |
| 4,936,016 | 6/1990 | Siimpson | 33/1 |

FOREIGN PATENT DOCUMENTS

| | | | |
|---|---|---|---|
| 0297775 | 1/1989 | European Pat. Off. | 73/53.05 |
| 9318 | 10/1955 | Fed. Rep. of Germany | 73/53.05 |
| 941520 | 4/1956 | Fed. Rep. of Germany | 73/53.05 |
| 2313998 | 9/1974 | Fed. Rep. of Germany | 73/53.07 |

*Primary Examiner*—Hezron E. Williams
*Assistant Examiner*—Joseph W. Roskos
*Attorney, Agent, or Firm*—Christensen, O'Connor, Johnson & Kindness

[57] ABSTRACT

An apparatus for analyzing lubricating oil is disclosed in the form of a test medium upon which an oil sample is placed, and comparative visual indicia which the user consults to provide a qualitative analysis of the oil sample. A method for the use of the apparatus is also disclosed.

12 Claims, 2 Drawing Sheets

30 32 34 36 38 40 42 44 46 48 50 52

LUBRICATING OIL ANALYSIS METHOD AND KIT

FIELD OF THE INVENTION

This invention relates to the analysis of lubricating oils, including a method for analysis of lubricating engine oil, and an apparatus for use in the method.

BACKGROUND OF THE INVENTION

Various means have been developed for use in analyzing characteristics of lubricating oils, including engine oils. In particular, methods and apparatus for testing the condition of oil and the sludge content of oil include chromatography and chemical analysis.

Other methods and apparatus for assessing the quality of used oil include placing a measured amount of oil upon an absorbent material, heating the sample, and awaiting dispersion of the sample. The amount of undispersed sludge may then be measured and rated quantitatively. These methods and apparatus, however, require significant controlled conditions, including measurement of the oil sample volume, and the use of a template to measure and rate the quantity of undispersed sludge in the sample. Additionally, these methods include heating of the sample, and awaiting dispersal of the sample. A need exists for a simple and rapid method of analyzing an oil sample on a qualitative basis.

SUMMARY OF THE INVENTION

It is an object of the present invention to provide a test of the quality of lubricating oil in the field that can be carried out rapidly, by untrained personnel, and without precision measurement of the sample. The lubricating oil may be of virtually any types, such as used in internal combustion engines, turbines, transmissions, etc. It is a further object of the invention to provide an apparatus to be used in the testing of the quality of the oil sample. Qualitative analysis of the oil sample includes determination of the dispersion of sludge within the oil by comparison to objective visual indicia.

These objectives are accomplished by providing to the user a test kit which includes an absorbent test medium upon which the oil is dispersed, a set of comparative visual indicia showing dispersed oils of various conditions with accompanying descriptive text, and instructions.

The test medium may be selected from a variety of absorbent media capable of receiving a sample of oil. The medium must permit separation of the sludge from the remainder of the sample. In other words, when placed upon a suitable medium, the sample will form a spot, approximately circular, consisting of an inner, darker circle of undispersed sludge, and an outer, lighter circle of oil.

The invention contemplates a kit containing, in addition to the test medium, a set of visual indicia depicting samples of lubricating oil disposed upon the test medium. The samples depicted are shown at different times following placement upon the medium, and show examples of oil in various conditions. At a minimum, the visual indicia should show a depiction of lubricating oil which is in an acceptable condition, and one of oil in an unacceptable condition. A greater range of conditions shown by the visual indicia will permit the test sample to be more closely approximated to the comparison examples by the kit user.

The invention further contemplates the inclusion, in the kit, of a descriptive text describing the condition of the comparison examples given in the visual indicia. A set of printed instructions is also included, to summarize the steps for use of the kit, which generally correspond to the description of the method given below.

The method for lubricating oil analysis toward which this invention is directed will comprise the steps of obtaining a sample of the oil, placing the sample upon the test medium, maintaining the test medium in a desired position for an effective period of time to develop a spot on the medium, visually comparing the spotted test medium against comparative visual indicia depicting lubricating oil in various conditions, and selecting the comparative example which most closely resembles the test medium spotted with the test sample.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
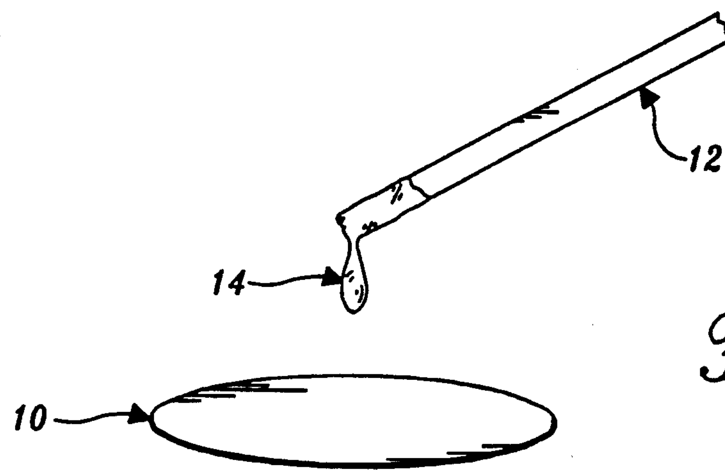
FIG. 1 is a pictorial view showing application of the test sample to the test medium.

The present invention provides a method and apparatus for analyzing the condition of lubricating oils. The oil may be of innumerable sources, including internal combustion engines, turbines, transmissions, differentials, pumps, etc. The apparatus itself contemplates a kit including a test medium, various comparative visual indicia with descriptive text, and instructions for the use of the kit in the oil analysis.

The analysis of used lubricating oil, for instance, engine oil, under this invention is essentially dependent upon the dispersion of oil on an absorptive medium. Oil, as it is used, develops contaminants including a component of sludge. When a sample of used oil is obtained and the sample is placed upon a suitably absorptive test medium, the component of sludge being of a greater molecular weight, will separate first from the remainder of the sample. The amount and coloration of the sludge and contaminants in the oil provide, when disposed upon the test medium, a means for qualitative analysis of the test sample, through comparison with depictions of oil in various conditions which have previously been disposed upon a similar test medium.

A. Test Medium

As indicated, the oil sample to be tested must be placed upon an appropriate test medium. Such test medium should result in rapid dispersion of the components of the oil sample, preferably within a few minutes and ideally within five minutes. Absorptive paper, such as chromatography paper, works well. Although chromatography paper typically is used for separation by adsorption, applicant's have found that such paper is highly effective for analyzing lubricating oil samples. The chromatography paper provides a consistent background which contrasts well with the oil sample and displays the coloration of the oil and the sludge. Other absortive/adsorptive papers, having the general physical properties and characteristics of chromatography paper will also be acceptable as long as such papers are of sufficiently consistent physical composition to provide accurate test results regardless of when the papers were manufactured. The preferred embodiment of the invention includes white colored chromatography paper.

It is to be understood that depending on the type of oil being analyzed and the particular lubricating purpose of the oil, for instance, whether for a gasoline powered engine as opposed to a diesel powered engine, the optimum test medium may need to be varied, whether the test medium is chromatography paper or other type of paper. The test medium may differ in its porosity, density, wicking ability, or other physical characteristic(s).

The shape of the test medium is unimportant, so long as it is of an effective size to permit dispersion of the oil sample, but small enough to be economical and limit waste. As discussed below, the oil sample need not be precisely measured; in general practice, the user will obtain the sample using a dipstick or other similar means. The typical sample size will be a single drop from the tip of the dipstick, thus, the test medium should be of a size to permit effective dispersion of the entire drop.

Referring to FIG. 1, a test medium 10 is disposed to receive a sample drop of oil to be tested 14 from the end of a dipstick 12. In a preferred embodiment of the invention, the test medium used is a piece of white colored chromatography paper measuring approximately 2.75 inches in diameter. A circular piece is preferably employed because the oil sample will disperse in a roughly circular pattern if maintained in a horizontal orientation during the test procedure. However, if the test medium is held in a vertical orientation during dispersion of the test sample, then other shapes of the test medium may be more appropriate.

Figure 2:
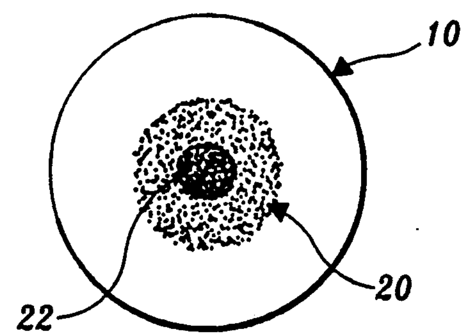
FIG. 2 is a plan view showing dispersion of the lubricating oil sample upon the test medium.

Referring to FIG. 2, a dispersion pattern of oil upon the test medium 10 is shown. The oil disperses into two major components, an outer ring 20 of oil and detergent and a darker inner ring 22, composed of heavier molecular weight contaminants and sludge.

B. Visual Indicia

Qualitative analysis of the test sample is accomplished by visual comparison of the completed test sample to visual indicia, provided as a part of the test kit. The visual indicia may be composed of an artistic rendering or a reproduction of a photograph of lubricating oil in various conditions. At a minimum, the visual indicia must include two representations of oil disposed upon the test media, one in unacceptable condition, and one in acceptable condition.

As more comparative examples are provided, however, the kit user may more easily determine a match between the test sample and the examples provided. If, however, too many examples are provided, the user must spend more time comparing the test sample to examples, and the difference in oil conditions shown on the examples may be too slight to provide any meaningful differentiation. Thus, an optimal number of examples will provide more gradations than a simple acceptable/unacceptable dichotomy, but will show oil in significantly different conditions.

Figure 3:
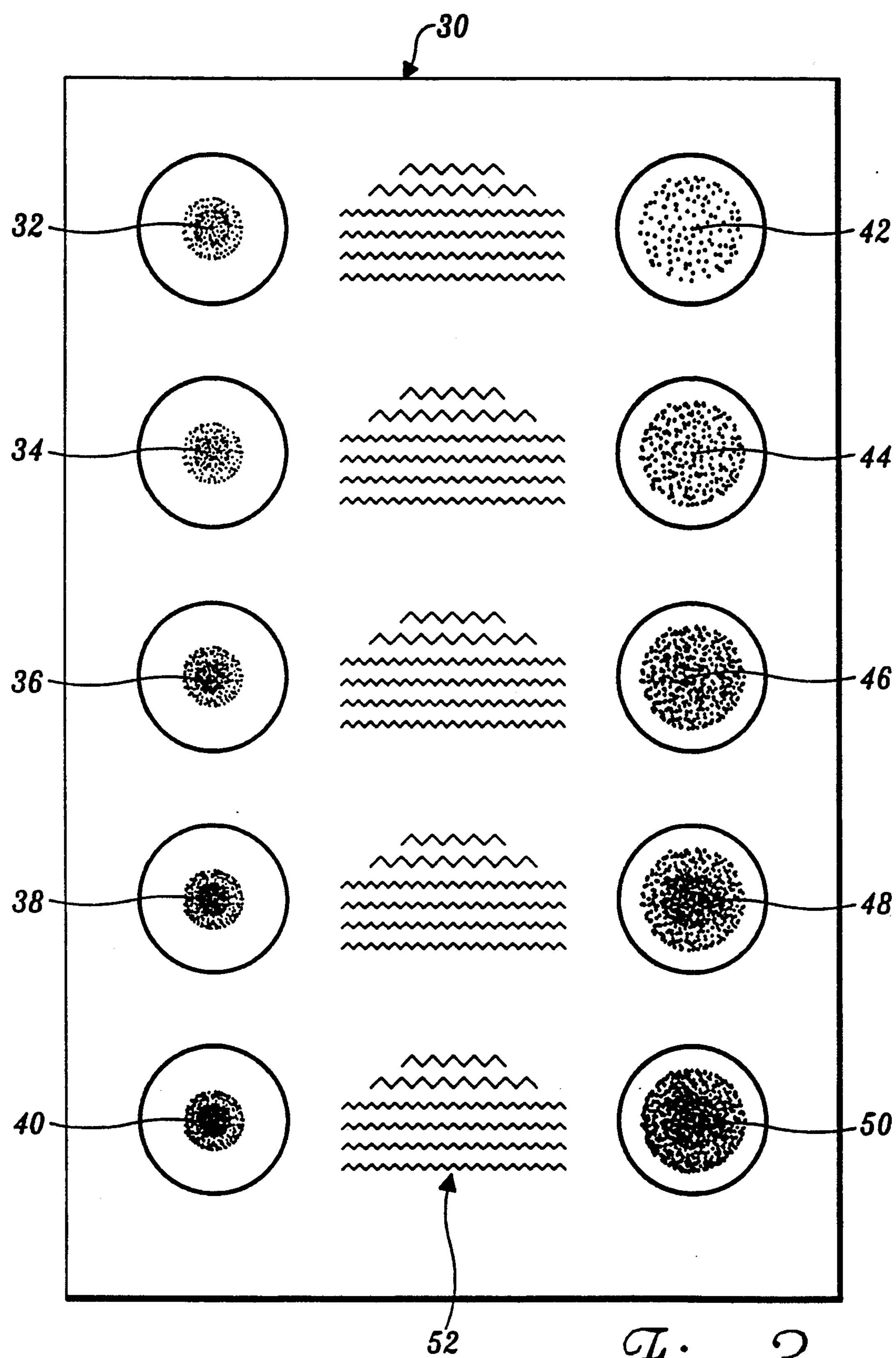
FIG. 3 is a top view showing the comparative visual indicia.

Referring to FIG. 3, a preferred embodiment of the visual indicia is shown. A printed sheet 30 contains depictions of examples of oil dispersed upon test media, the oil having these characteristics: dispersion of oil in excellent condition after five minutes, 32, and after 12 hours, 42; oil in good condition, acceptable within the normal range for typical engine oil, after 5 minutes, 34, and after 12 hours, 44; oil at the limit of useful life, requiring an oil change, after 5 minutes, 36, and after 12 hours, 46; oil in an unacceptable condition, indicating an oil change overdue, after 5 minutes, 38, and after 12 hours, 48; oil in seriously poor condition, indicating possible equipment damage, after 5 minutes, 40, and after 12 hours, 50. A descriptive text 52 corresponding to each of these examples is likewise provided.

It is preferable that the examples depicted be dispersed upon the same medium provided in the kit, to assure that the kit user compares the sample to be tested to examples produced under similar conditions.

It is to be understood that a different number of indicia than shown in FIG. 3 may be provided. Also, the visual indicia may represent dispersion of oil samples at time durations other than as shown in FIG. 3.

C. Test Method

The method contemplated in this invention for the analysis of lubricating oil is effective but simple, and has the advantage of quickness and ease of use in uncontrolled conditions by untrained personnel. It comprises the steps of (a) obtaining a sample of the used lubricating oil, (b) placing the sample upon an absorbent test medium, (c) maintaining the test medium in a desired position for a sufficient period of time to develop a spot on the test medium, (d) making a visual comparison of the spotted test medium against comparative visual indicia depicting lubricating oil in various conditions, and (e) selecting the example from the comparative indicia which most closely resembles the test sample.

It is not necessary that the sample be taken during actual operation of the engine or other equipment in order to obtain a representative sample of oil. The sample may be taken at any time before, during or after operation of the engine or equipment being lubricated. Under ordinary circumstances, the sample may be obtained using a dipstick provided as a part of the engine, transmission or other equipment under lubrication. The user will withdraw an amount of oil along with the dipstick, which will collect into a drop, which is then placed upon the absorbent test medium.

Once the oil has been placed on the test medium, it will begin to disperse. In order to provide an effective comparison, the test medium should be kept in a desired position. Such position could be, for example, horizontal, vertical, etc. as long as the position coincides with the comparative visual indicia. Complete contact between the test medium and an underlying surface should, however, be avoided, as this contact may affect the dispersal of the test sample.

The user permits dispersal of the sample for a time corresponding to the control examples provided in the comparative visual indicia. Next, the user carefully compares the sample to the examples, and selects the nearest match. Finally, the user consults the descriptive text accompanying the example selected to determine the condition of the oil used in the example.

While the preferred embodiment of the invention has been illustrated and described, it will be appreciated that various changes can be made therein without departing from the spirit and scope of the invention, with the scope of the present invention being defined by the following claims.

The embodiments of the invention in which an exclusive property or privilege is claimed are defined as follows:

1. A test kit for the analysis of lubricating oil, comprising:

a test medium capable of absorbing the oil;

a plurality of comparative visual indicia depicting at least two different conditions of lubricating oil disposed upon said test medium; and a descriptive text corresponding to said comparative visual indicia.

2. A test kit as recited in claim 1, wherein said test medium is composed of paper of a porosity and density to provide rapid dispersion of the lubricating oil.

3. A test kit as recited in claim 1, wherein said comparative visual indicia are selected from the group consisting of photographs and artistic renditions of used lubricating oil in various conditions.

4. A test kit as recited in claim 3, wherein said visual indicia comprise:

a depiction of lubricating oil in acceptable condition, disposed upon said test medium; and a depiction of lubricating oil in unacceptable condition, disposed upon said test medium.

5. A test kit as recited in claim 3, wherein said visual indicia comprise depictions of lubricating oil dispersed on the test medium for specific lengths of time.

6. The test kit of claim 1, wherein each of the visual indicia depicts an inner, darker area of sludge and an outer, lighter area of oil.

7. The test kit of claim 1, wherein the test medium is discrete from the plurality of comparative visual indicia.

8. A method for analysis of lubricating oil, comprising the steps of:

obtaining a sample of said lubricating oil;

disposing said sample upon a test medium capable of absorbing said lubricating oil;

maintaining said test medium in a selected position for an effective time to develop a spot on said test medium;

visually comparing said spotted test medium against a plurality of comparative visual indicia depicting lubricating oil in at least two different conditions; and, selecting one of the plurality of comparative indicia which most closely resembles said spotted test medium.

9. A method as recited in claim 8, wherein said test medium is composed of paper of a porosity and density to provide rapid dispersion of the lubricating oil.

10. A method as recited in claim 8, wherein said comparative visual indicia are selected from the group consisting of photographs and artistic renditions of used lubricating oil.

11. A method as recited in claim 10, wherein said visual indicia comprise:

a depiction of lubricating oil in acceptable condition, disposed upon said test medium; and a depiction of lubricating oil in unacceptable condition, disposed upon said test medium.

12. A test kit for the analysis of lubricating oil, comprising:

a test medium capable of absorbing the oil;

a first visual indicium depicting lubricating oil in acceptable condition;

a second visual indicium depicting lubricating oil at the limit of useful life, indicating an oil change is due;

a third visual indicium depicting lubricating oil in a condition indicating an oil change is overdue; and descriptive means corresponding to the first, second, and third visual indicia for informing a user of the particular condition of the lubricating oil.

* * * * *